(12) United States Patent
Housman (10) Patent No.: US 8,986,347 B2
(45) Date of Patent: Mar. 24, 2015

(54) KNOTLESS SUTURE ANCHOR

(71) Applicant: Mark Edwin Housman, North Attleborough, MA (US)

(72) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/297,056

(22) Filed: Jun. 5, 2014

(65) Prior Publication Data

US 2014/0288598 A1 Sep. 25, 2014

Related U.S. Application Data (62) Division of application No. 13/251,429, filed on Oct. 3, 2011, now Pat. No. 8,764,798.

(51) Int. Cl.
*A61B 17/04* (2006.01)

(52) U.S. Cl.
CPC ..... *A61B 17/0401* (2013.01); *A61B 2017/0409* (2013.01); *A61B 2017/0414* (2013.01); *A61B 2017/0427* (2013.01); *A61B 2017/0448* (2013.01)
USPC .......................................... 606/232; 606/300

(58) Field of Classification Search
CPC ................. A61B 2017/0448; A61B 2017/045; A61B 2017/0451; A61B 17/0401
USPC ......................................................... 606/232
See application file for complete search history.

(56) References Cited

U.S. PATENT DOCUMENTS

| | | | |
|---|---|---|---|
| 4,901,721 A | 2/1990 | Hakki | |
| 5,671,505 A | 9/1997 | Anscher | |
| 5,827,291 A | 10/1998 | Fucci et al. | |
| 5,948,000 A | 9/1999 | Larsen et al. | |
| 6,648,903 B1 | 11/2003 | Pierson, III | |
| 7,390,329 B2 | 6/2008 | Westra et al. | |
| 8,764,798 B2 * | 7/2014 | Housman | 606/232 |
| 2002/0052630 A1 | 5/2002 | Morgan et al. | |
| 2004/0167546 A1 * | 8/2004 | Saadat et al. | 606/144 |
| 2005/0055052 A1 | 3/2005 | Lombardo et al. | |
| 2005/0090827 A1 * | 4/2005 | Gedebou | 606/72 |
| 2005/0245932 A1 * | 11/2005 | Fanton et al. | 606/72 |
| 2005/0256530 A1 | 11/2005 | Petros | |
| 2006/0106423 A1 | 5/2006 | Weisel et al. | |
| 2007/0112385 A1 | 5/2007 | Conlon | |
| 2008/0103528 A1 | 5/2008 | Zirps et al. | |
| 2010/0063542 A1 | 3/2010 | van der Burg et al. | |

(Continued)

*Primary Examiner* — Elizabeth Houston
*Assistant Examiner* — Todd J Scherbel
(74) *Attorney, Agent, or Firm* — Burns & Levinsond, LLP; Joseph M. Maraia (57) ABSTRACT

Methods and apparatus described herein provide for a knotless suture anchor that captures and secures a suture by pinching on an inserted suture with a flexible element disposed within the knotless suture anchors body. The knotless suture anchor has an integrated flexible element that is formed as a plastic part within the knotless suture anchor's body. The free end of the flexible element terminates near a suture eyelet and can be compressed by a driver rod that is inserted into the knotless suture anchor to allow for insertion of a suture. With the flexible element compressed by the driver rod, the suture can be passed through the eyelet(s). When the driver rod is withdrawn, the flexible element expands thereby pinching the suture against the eyelet(s). If the driver rod is reinserted, the flexible element is recompressed and the suture can thereby be released or adjusted.

10 Claims, 6 Drawing Sheets

(56) References Cited

U.S. PATENT DOCUMENTS

| | | |
|---|---|---|
| 2011/0004242 A1 | 1/2011 | Stchur |
| 2011/0004243 A1 | 1/2011 | Dreyfuss |
| 2013/0085529 A1* | 4/2013 | Housman ............... 606/232 |

* cited by examiner

KNOTLESS SUTURE ANCHOR

REFERENCE TO PENDING PRIOR PATENT APPLICATIONS

This patent application is a divisional of U.S. patent application Ser. No. 13/251,429, filed Oct. 3, 2011, issued as U.S. Pat. No. 8,764,798 on Jul. 1, 2014, which is incorporated by reference in its entirety herein.

BACKGROUND

Suture anchors are generally comprised of the following basic parts: an anchor, an eyelet and a suture. The anchor is the portion that can be inserted into the bone. The anchor may be a screw mechanism and made of metal or biodegradable material that can dissolve in the body over time. The eyelet is a hole or a loop in the anchor to through which the suture passes thereby linking the anchor to the suture. Conventional suture anchors secure a suture by securing the suture by an internal screw plug, capturing the suture via friction between a bone tunnel and an implant and capturing the suture through one-way slip knots.

SUMMARY

Configurations herein substantially overcome shortcomings of conventional suture anchors by providing a knotless suture anchor that captures and secures a suture by pinching on an inserted suture against a suture slot (such as an eyelet) with a flexible element disposed within the knotless suture anchor's body. In one embodiment, the knotless suture anchor has an integrated flexible element that is formed as a plastic part within the knotless suture anchor's body. The free end of the flexible element terminates near a suture eyelet and can be compressed by a driver rod that is inserted into the knotless suture anchor to allow for insertion of a suture. With the flexible element compressed by the driver rod, the suture can be passed through the eyelet(s). When the driver rod is withdrawn, the flexible element expands thereby pinching the suture against the eyelet(s). If the driver rod is reinserted, the flexible element is recompressed and the suture can thereby be released or adjusted.

The knotless suture anchor described herein includes at least one suture slot and a flexible element (such as the spring element) compressible away from the at least one suture slot. The flexible element can also be expandable toward the at least one suture slot. The knotless suture anchor also includes at least one barb extending from an external surface of the suture anchor. During utilization of the knotless suture anchor, a flexible element of the knotless suture anchor's body becomes compressed to allow for threading of the suture through the knotless suture anchor's body via a suture reception portion of the knotless suture anchor's body. Upon releasing the flexible element from a state of compression, the flexible element expands toward the suture reception portion and the suture is secured between the expanded flexible element i and the suture reception portion of the knotless suture anchor's body.

In one embodiment of the knotless suture anchor, the flexible element comprises a spring element that is formed (or molded) as part of a body of the knotless suture anchor. In other words, the spring element is an outgrowth of a portion of the body of the knotless suture anchor itself. For example, the knotless suture anchor can have a bone insertion tip formed as a distal portion of the body of the knotless suture anchor, whereby the bone insertion tip is formed as a base for the spring element and the spring element is disposed within the body the knotless suture anchor.

A proximal end of the spring element is substantially located near the at least one suture slot when the spring element is fully expanded. The proximal end of the spring element allows a suture to be threaded through the at least one suture slot when the spring element is compressed. To secure the suture within the knotless suture anchor, the spring element expands towards the at least one suture slot and the suture becomes pinched between the proximal end of the spring element and at least one edge of the at least one suture slot. It is understood that various embodiments of the knotless suture anchor (or parts of the knotless suture anchor) need not be limited to being formed in plastic.

BRIEF DESCRIPTION OF THE DRAWINGS

The foregoing and other objects, features and advantages of the invention (i.e. the knotless suture anchor) will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Methods and apparatus described herein provide for a knotless suture anchor that captures and secures a suture by pinching on an inserted suture with a flexible element disposed within the knotless suture anchors body. The knotless suture anchor has an integrated flexible element that is formed as a plastic part within the knotless suture anchor's body. The free end of the flexible element terminates near a suture eyelet and can be compressed by a driver rod that is inserted into the knotless suture anchor to allow for insertion of a suture. With the flexible element compressed by the driver rod, the suture can be passed through the eyelet(s). When the driver rod is withdrawn, the flexible element expands thereby pinching the suture against the eyelet(s). If the driver rod is reinserted, the flexible element is recompressed and the suture can thereby be released or adjusted. It is noted that, in various embodiments, the flexible element can be a helical coil spring element or a zig-zag spring element. However, the flexible element is not limited only to spring element embodiments.

Figure 1:
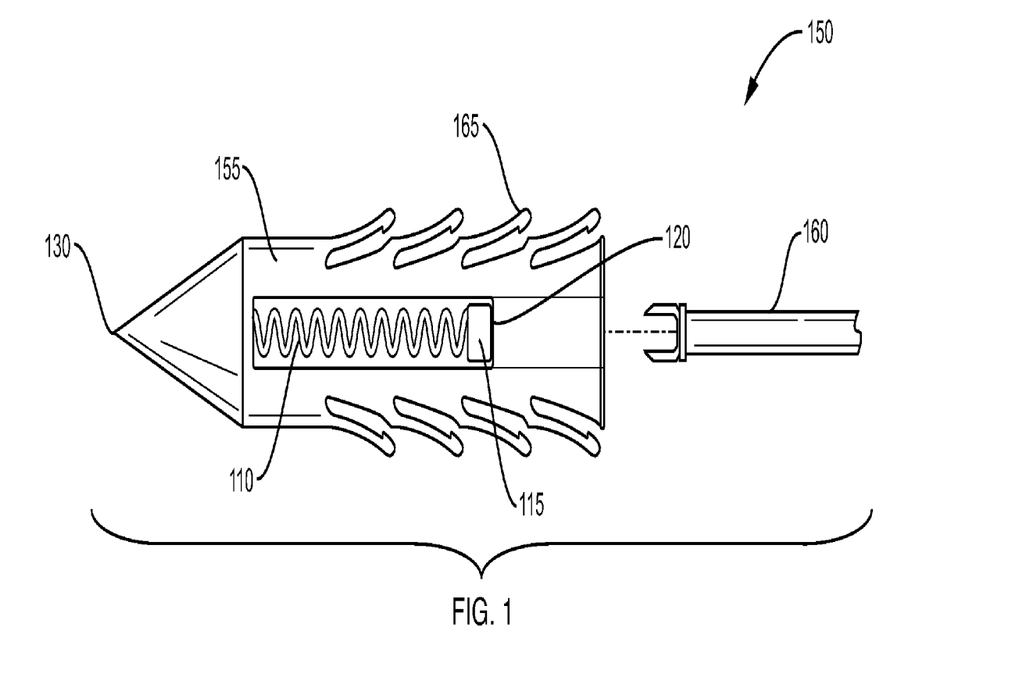
FIG. 1 shows a perspective view of a knotless suture anchor with an expanded spring element prior to insertion of a driver rod into the knotless suture anchor according to embodiments herein.

FIG. 1 shows a perspective view of a knotless suture anchor 150 with an expanded spring element 110 prior to insertion of a driver rod 160 into the knotless suture anchor 150 according to embodiments herein.

The body 155 of the knotless suture anchor 150 includes at least one suture slot 120 through which a suture can be threaded. A flexible element, such as the spring element 110, is disposed within the body 155 of the knotless suture anchor 150. The spring element 110 is compressible away from the at least one suture slot 120 and expandable toward the at least one suture slot 120. At least one barb 165 extends from an external surface of the knotless suture anchor 150. In the alternative, the external surface of the knotless suture anchor 150 can provide at least one screw thread or any other feature that would allow for introduction of the anchor 150 into the bone and/or fixation of the anchor to the bone.

In one embodiment, the spring element 110 can be molded as part of the body 155 of the knotless suture anchor 150. An insertion tip 130 of the knotless suture anchor acts as a base of the spring element 110, which extends from insertion tip 130 and toward the at least one suture slot 120. A proximal end 115 of the spring element 110 substantially situated near an edge of the at least one suture slot 120 when the spring element is expanded. It is understood that in various embodiments the insertion tip 130 can be a bone insertion tip. In addition, it is understood that, in various embodiments, the flexible element need not be molded as part of the body 155 of the knotless suture anchor 150. Thus, the flexible element (such as the spring element) can be integrated into the body 155 of the knotless suture anchor 150 in any manner.

Figure 2:
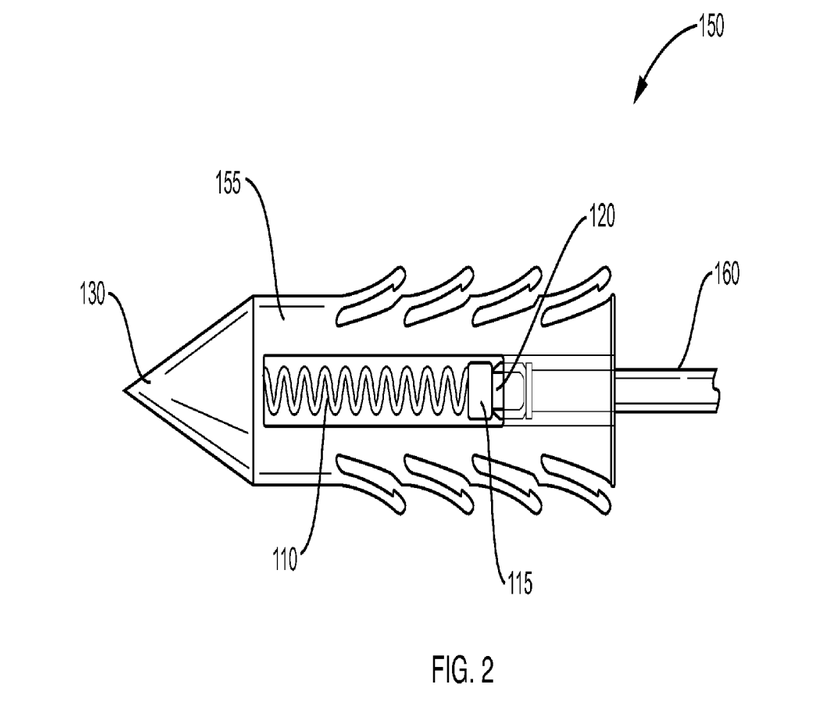
FIG. 2 shows a perspective view of a driver rod inserted into a knotless suture anchor in order to compress a spring element disposed within the knotless suture anchor's body according to embodiments herein.

FIG. 2 shows a perspective view of a driver rod 160 inserted into a knotless suture anchor 150 in order to compress a spring element 110 disposed within the knotless suture anchor's body 155 according to embodiments herein.

The driver rod 160 is inserted into the knotless suture anchor 150 to press against the proximal end 115 of the spring element 110. The proximal end 115 of the spring element 110 allows a suture to be threaded through the at least one suture slot 120 when the spring element 110 is compressed (1) away from the at least one suture slot 120 and (2) toward the insertion tip 130. A suture can be secured between the proximal end 115 of the spring element 110 and the at least one suture slot 120 when the spring element 110 is expanded toward the at least one suture slot 120

Figure 3:
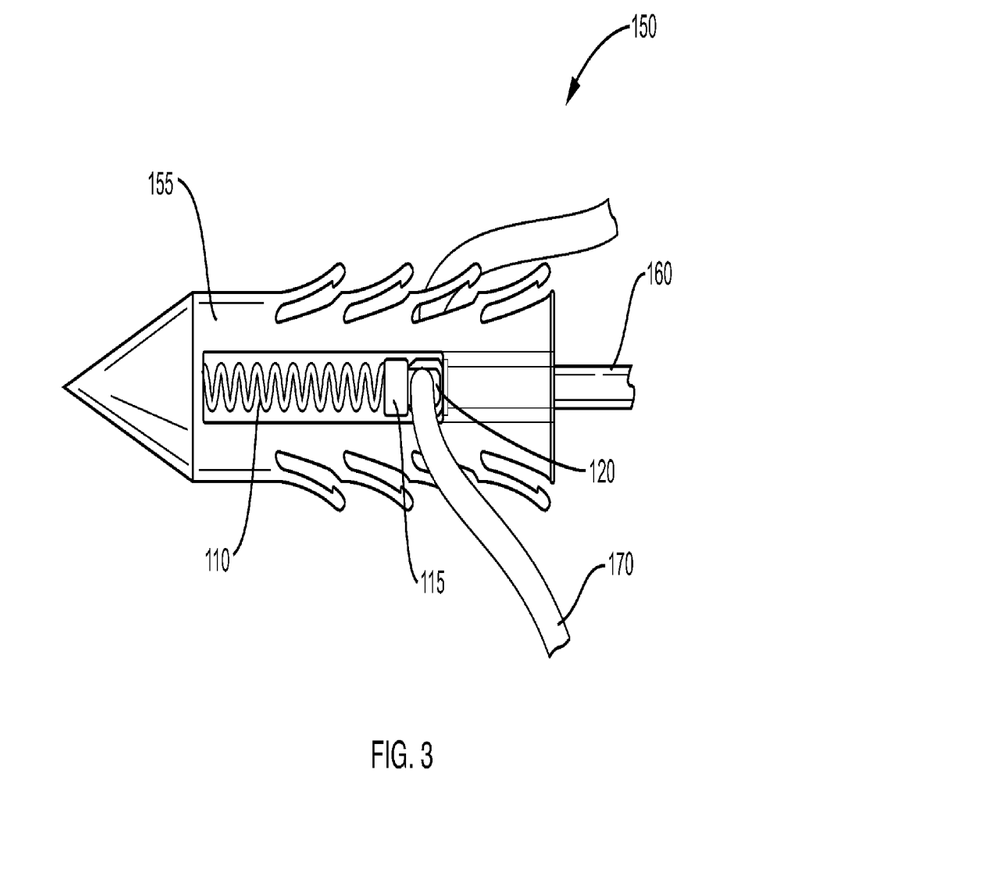
FIG. 3 shows a perspective view of a suture threaded through respective suture slots while a spring element is compressed according to embodiments herein.

FIG. 3 shows a perspective view of a suture 170 threaded through respective suture slots 120 while a spring element 110 is compressed according to embodiments herein.

In one embodiment, the knotless suture anchor 150 can have multiple suture slots, wherein each respective suture slot 120 is formed as part of a body 155 of the knotless suture anchor 150. A first end of a suture 170 can enter the body 155 of the knotless suture anchor 150 via a first suture slot and exit the body 155 of the knotless suture anchor 150 via the second suture slot while the spring element 110 is compressed away from the respective first and second suture slots by the driver rod 160. The suture 170 can be threaded through the body 155 of the knotless suture anchor 150 by being passed between the proximal end 115 of the compressed spring element 110 and the driver rod 160.

Figure 4:
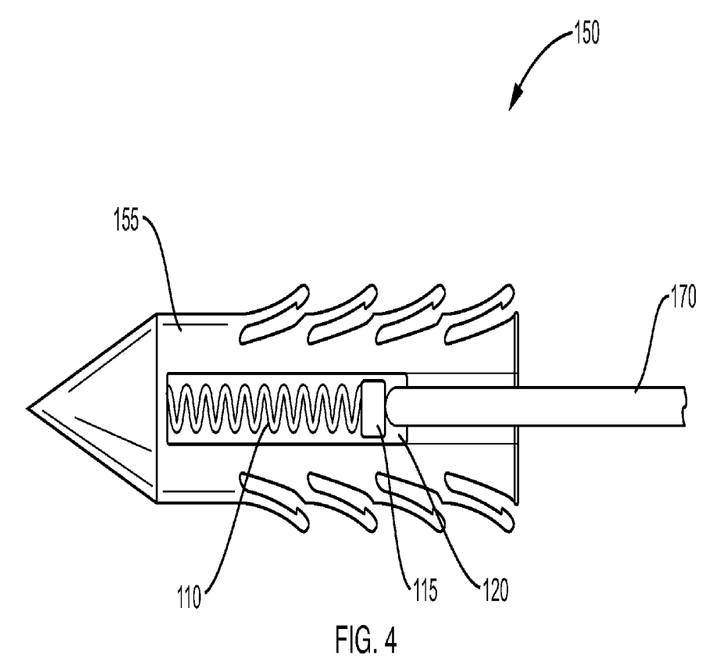
FIG. 4 shows a perspective view of a suture secured within a knotless suture anchor by way of an expanded spring element pinching the suture against respective suture eyelets according to embodiments herein.

FIG. 4 shows a perspective view of a suture 170 secured within a knotless suture anchor 150 by way of an expanded spring element 110 pinching the suture 170 against respective suture eyelets 120 according to embodiments herein.

The driver rod 160 can be removed from the knotless suture anchor 150 to allow the spring element 110 to expand. The proximal end 115 of the expanded spring element 110 is situated substantially near the at least one suture slot 120. With the suture 170 having been threaded through the at least one suture slot 120 and over the proximal end 115 of the spring element 110 when the spring element 110 was compressed by the driver rod 160, the suture 170 is thereby secured within the body 155 of the knotless suture anchor 150 by being pinched between the proximal end 115 of the expanded spring element 110 and the at least one suture slot 120.

Figure 5:
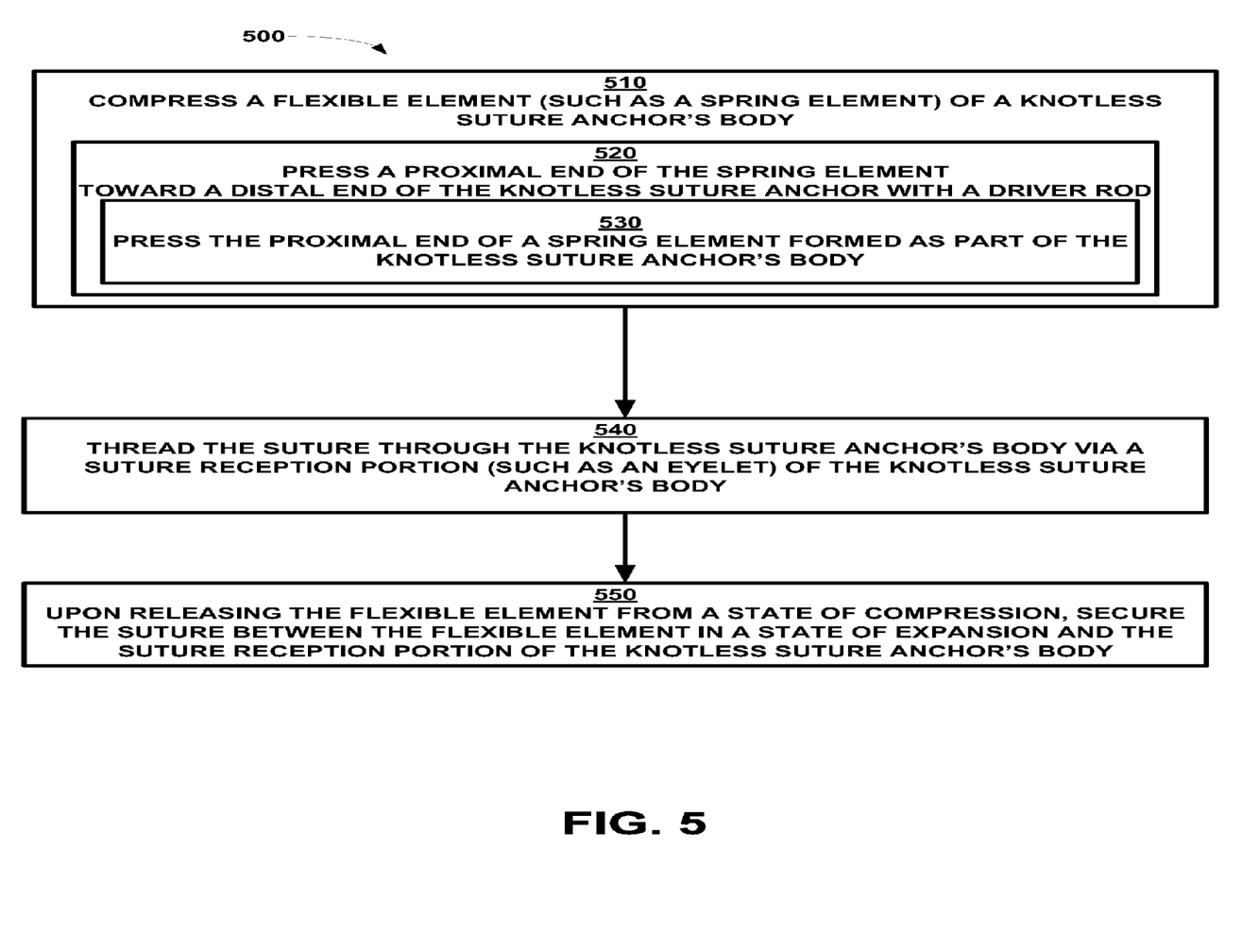
FIG. 5 is a flowchart of steps performed to secure a suture within a knotless suture anchor by compressing and expanding a spring element disposed within the knotless suture anchor according to embodiments herein.

FIG. 5 is a flowchart 500 of steps performed to secure a suture 170 within a knotless suture anchor 150 by compressing and expanding a spring element 110 disposed within the knotless suture anchor 150 according to embodiments herein.

At step 510, compress a flexible element of a knotless suture anchor's body 155. The flexible element can be a spring element 110 formed as a part of the knotless suture anchor's body 155. In another embodiment, the spring element 110 can be a separate structure attached to the knotless suture anchor's body 155. It is understood that embodiments of the knotless suture anchor 150 are not limited to a spring element 110. Rather, the flexible element can be any element that can be adjusted so as to allow for insertion of a suture 170 and subsequently readjusted so as to secure the suture 170 to the knotless suture anchor's body 155 without requiring the creation of a knot in the suture 170.

At step 520, press a proximal end 115 of a spring element 110 toward a distal end of the knotless suture anchor 150 with a driver rod 160. The driver rod 160 can have a tip designed to press against the spring element 110 while maintaining a space between the proximal end 115 of the spring element 110 and the tip driver rod 160. A suture 170 can thereby be passed through the space created between the proximal end 115 of the spring element 110 and the tip of driver rod 160.

At step 530, press the proximal end 115 of a spring element 110 formed as part of the knotless suture anchor's body 155. It is noted that, in some embodiments, a base of the spring element 110 comprises a distal insertion tip 130 of the knotless suture anchor 150. The distal insertion tip 130 can be any kind of suture anchor tip designed to be inserted into bone, tissue, tendon, muscle or any other anatomical structure.

At step 540, thread the suture 170 through the knotless suture anchor's body 155 via a suture reception portion of the knotless suture anchor's body 155. The suture reception portion can be an eyelet and the knotless suture anchor 150 can have multiple eyelets formed on knotless suture anchor's body 155. The suture 170 is threaded through the respective eyelets and (as described at step 520) passed through the space between the proximal end 115 of the spring element 110 and the tip of driver rod 160.

At step 550, upon releasing the flexible element from a state of compression, secure the suture 170 between the flexible element in a state of expansion and the suture reception portion of the knotless suture anchor's body 155. For example, the spring element 110 expands towards the respective eyelets as the driver rod 160 is withdrawn from the knotless suture anchor's body 155. Once the spring element 110 is fully expanded, the proximal end 115 of the spring element 110 is substantially near the respective eyelets and the portion of the suture 170 disposed within the knotless suture anchor's body 155 is pinched (i.e. secured) between the eyelets and the proximal end 115 of the expanded spring element 110.

Figure 6:
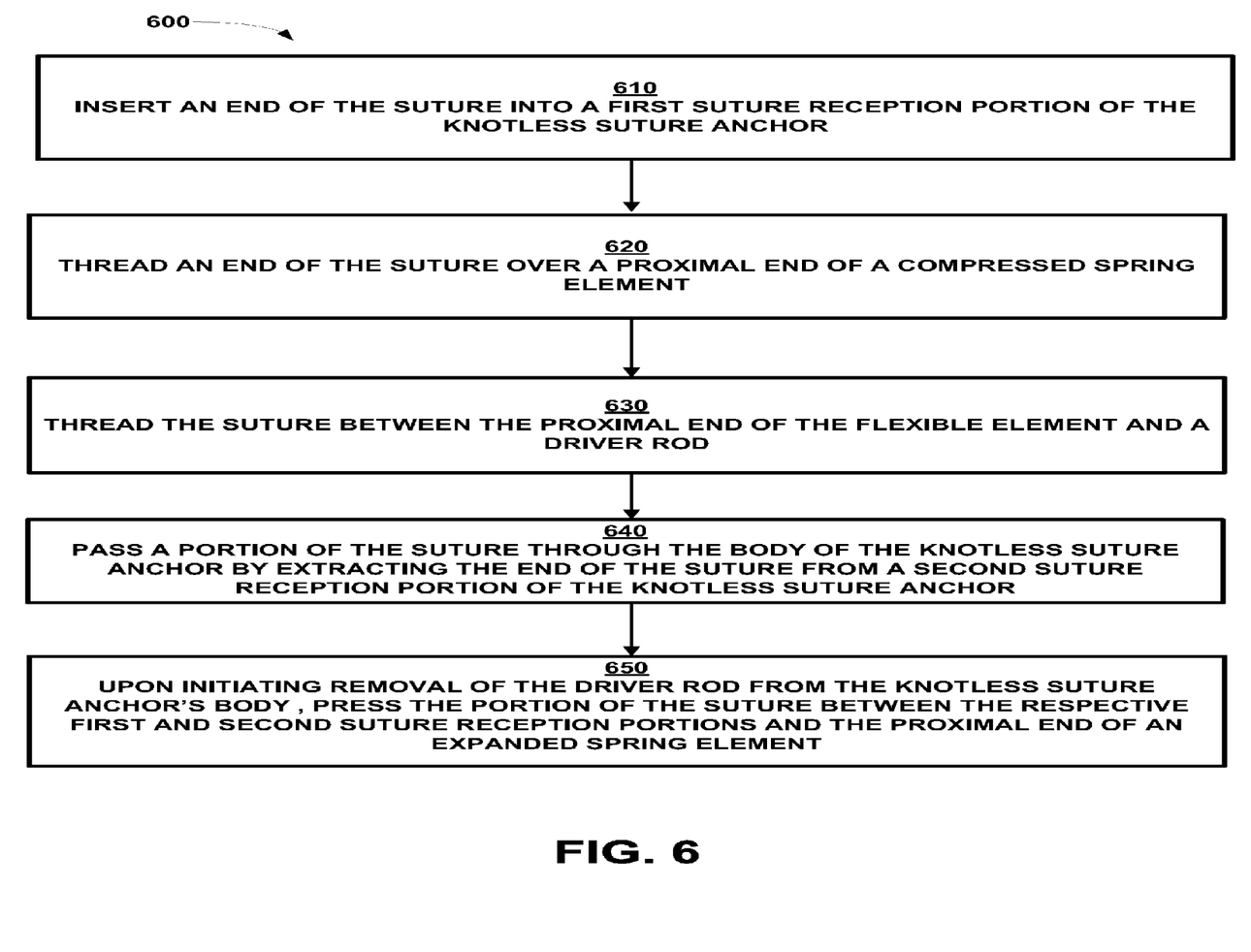
FIG. 6 is a flowchart of steps performed to press a suture between suture reception portions of the knotless suture anchor's body and a proximal end of an expanded spring element according to embodiments herein.

FIG. 6 is a flowchart 600 of steps performed to press a suture 170 between suture reception portions of the knotless suture anchor's body 155 and a proximal end 115 of an expanded spring element 110 according to embodiments herein.

At step 610, insert an end of the suture 170 into a first suture reception portion of the knotless suture anchor. For example, once the knotless suture anchor 150 has been inserted into an anatomical structure, a free end of a suture 170 can enter the knotless suture anchor's body 155 by being passed through a first suture eyelet.

At step 620, thread an end of the suture 170 over a proximal end 115 of a compressed spring element 110. The spring element 110 can be in a state of compression due to a driver rod 160 having been inserted into the knotless suture anchor 150 to compress the spring element 110 away from suture eyelets provided by the knotless suture anchor 150.

At step 630, thread the suture 170 between the proximal end 115 of the flexible element and a driver rod 160. The tip of the driver rod 160 that presses against the proximal end 115 of the spring element 110 can be shaped in order to create a space between the tip of the driver rod 160 and the proximal end 115 of the spring element 110. The suture 170 can thereby be passed through this space and pulled toward a second eyelet.

At step 640, pass a portion of the suture 170 through the body of the knotless suture anchor 150 by extracting the end of the suture 170 from a second suture reception portion of the knotless suture anchor 150.

At step 650, upon initiating removal of the driver rod 160 from the knotless suture anchor's body 155, press the portion of the suture 170 between the respective first and second suture 170 reception portions and the proximal end 115 of an expanded spring element 110.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A method for securing at least a portion of a suture to a suture anchor, the method comprising:
providing a suture anchor body including an internal cavity and a flexible member housed within the internal cavity, the flexible member including a spring element and a suture engagement element, proximal end of the spring element mechanically attached to the suture engagement element, the suture engagement element positioned in close proximity to a proximal edge of at least one suture slot when the spring element is in an uncompressed state, and a distal end of the spring element coupled to a distal portion of the internal cavity, the spring element comprising one from a group comprising: a helical coil spring element; and a zig-zag spring element, a distal end of the suture anchor body including an insertion tip, wherein the at least one suture slot is formed longitudinally in the body;
threading the suture through the suture anchor body via the suture slot
inserting a driver rod in the internal cavity and compressing the flexible member; and
upon releasing the flexible member from a state of compression, securing the suture between the flexible member in a state of expansion and the suture slot;
wherein at least one barb extends from an external surface of the suture anchor.

2. The method as in claim 1, wherein compressing the flexible member of the suture anchor body includes: pressing a proximal end of the spring element towards a distal end of the suture anchor with a driver rod.

3. The method as in claim 2, pressing the proximal end of the spring element includes: pressing a proximal end of a spring element formed as part of the suture anchor body, wherein a base of the spring element comprises a distal insertion tip of the suture anchor.

4. The method as in claim 1, wherein threading the suture through the suture anchor body via a suture reception portion of the suture anchor body includes: inserting an end of the suture into a first suture reception portion of the suture anchor; threading an end of the suture over a proximal end of the flexible member in the state of compression; and passing at least a portion of the suture through the body of the suture anchor by extracting the end of the suture from a second suture reception portion of the suture anchor.

5. The method as in claim 4, wherein threading the end of the suture over the proximal end of the flexible member includes: threading at least the portion of the suture between the proximal end of the flexible member and a driver rod, the driver rod inserted into the suture anchor body to compress a spring element toward a distal insertion tip of the suture anchor.

6. The method as in claim 5, wherein securing the suture between the flexible member in the state of expansion and the suture reception portion of the suture anchor body includes: upon initiating removal of the driver rod from the suture anchor body, pressing the portion of the suture between the respective first and second suture reception portions of the suture anchor body and the proximal end of the flexible member, wherein the flexible member is in an expanded state due to removal of the driver rod.

7. The method as in claim 5, comprising: wherein inserting the end of the suture into the first suture reception portion of the suture anchor includes: inserting the end of the suture into a first suture slot formed as part of the suture anchor body; and wherein extracting the end of the suture from the second suture reception portion of the suture anchor includes: extracting the end of the suture from a second suture slot formed as part of the suture anchor body.

8. The method as in claim 1, wherein compressing the flexible member of the suture anchor body includes selecting from a group consisting of: compressing a zig-zag spring element disposed within the suture anchor body, the zig-zag spring element formed as part of the suture anchor body; and compressing a helical coil spring element disposed within the suture anchor body, the helical coil spring element formed as part of the suture anchor body.

9. The method as in claim 1, comprising: inserting a distal insertion tip of the suture anchor into a portion of an anatomical structure, the suture anchor secured to a portion of bone via at least one barb extending from an external surface of the suture anchor.

10. The method as in claim 9, comprising: wherein threading the suture through the suture anchor body via a suture reception portion of the suture anchor body includes: passing at least a portion of the suture (1) between a respective first and second suture slot formed as part of the suture anchor body and (2) over a spring element compressed away from the respective first and second suture slots; and wherein securing the suture includes: releasing the spring element to an expanded state; and capturing the portion of the suture between the respective first and second suture slots and end of the spring element, the suture anchor comprising an insertion tip comprising a base of the spring element, the spring element formed as part of the suture anchor body.

* * * * *